US009549257B2

(12) United States Patent
Hall et al.

(10) Patent No.: US 9,549,257 B2
(45) Date of Patent: Jan. 17, 2017

(54) FEEDBACK CANCELLATION FOR VEHICLE COMMUNICATIONS SYSTEM

(71) Applicant: Pinnacle Peak Holding Corporation, Austin, TX (US)

(72) Inventors: Steve B. Hall, Austin, TX (US); James P. Roberts, Austin, TX (US); Samuel W. Grove, Austin, TX (US)

(73) Assignee: Pinnacle Peak Holdings Corporation, Austin, TX (US)

( * ) Notice: Subject to any disclaimer, the term of this patent is extended or adjusted under 35 U.S.C. 154(b) by 299 days.

(21) Appl. No.: 14/227,138

(22) Filed: Mar. 27, 2014

(65) Prior Publication Data

US 2014/0294198 A1 Oct. 2, 2014

Related U.S. Application Data

(60) Provisional application No. 61/805,693, filed on Mar. 27, 2013.

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04R 3/02*** | (2006.01) |
| *H04R 1/10* | (2006.01) |
| *H04R 3/12* | (2006.01) |
| *H04R 5/02* | (2006.01) |

(52) U.S. Cl.

CPC ............... *H04R 3/02* (2013.01); *H04R 1/1083* (2013.01); *H04R 3/12* (2013.01); *H04R 5/023* (2013.01); *H04R 2410/05* (2013.01); *H04R 2499/13* (2013.01)

(58) Field of Classification Search

CPC ..................... G10K 11/178; G10K 2210/1282; H04R 2499/13; H04R 3/002; H04R 3/005; H04R 1/1083; H04R 2227/001; H04R 2420/01

USPC ....................... 381/71.4, 73.1, 86, 94.7, 94.9

See application file for complete search history.

(56) References Cited

U.S. PATENT DOCUMENTS

| | | | | |
|---|---|---|---|---|
| 8,126,492 B2 | 2/2012 | Hannosh et al. | | |
| 2007/0135061 A1* | 6/2007 | Buck | H04M 1/6083 | 455/73 |
| 2010/0035663 A1* | 2/2010 | Haulick | H04M 1/6083 | 455/569.2 |
| 2012/0070013 A1* | 3/2012 | Vau | G10K 11/178 | 381/71.4 |

* cited by examiner

*Primary Examiner* — Alexander Jamal

(74) *Attorney, Agent, or Firm* — Faegre Baker Daniels LLP

(57) ABSTRACT

The present disclosure relates to a system and method of cancelling feedback in a vehicle communications system. The system and method may adjust a phase and a polarity of the microphone signal to produce an inverted microphone signal having a shifted phase. A speaker signal may be summed with the inverted microphone signal to cancel out at least a portion of a microphone signal component of the speaker signal.

20 Claims, 7 Drawing Sheets

FEEDBACK CANCELLATION FOR VEHICLE COMMUNICATIONS SYSTEM

CROSS-REFERENCE TO RELATED APPLICATIONS

This application claims priority to U.S. Provisional Application No. 61/805,693, filed Mar. 27, 2013, the entire disclosure of which is expressly incorporated by reference herein.

FIELD OF THE DISCLOSURE

The present disclosure relates to vehicle communications systems, and more particularly to a system and method for feedback cancellation for a vehicle communications system.

BACKGROUND

Vehicles in industrial and public safety applications have had intercom/radio mixer systems for many decades. These systems allow the vehicle users to communicate amongst themselves and also communicate to distant individuals using mobile radio technology. The systems have often incorporated headsets due to loud ambient noise environments inside and outside the vehicle. These systems aim to provide more coherent communication in the vehicle.

Some of these vehicle communication systems utilize headsets. Headsets may introduce some potential drawbacks including the additional time to don the headset, comfort, and restriction of movement. The donning of headsets takes additional time when entering the vehicle. In particular, for public safety workers, every second counts when trying to get as quickly as possible to the scene of an emergency. Even the couple of seconds that it takes to find and don a headset can be distracting and have a negative effect on the outcome of a life threatening situation. Headsets may become uncomfortable depending on the design and length of time that a particular headset is worn. If uncomfortable, crewmembers may decide not to wear the headsets, thereby exposing crewmembers to the inability to effectively communicate over the vehicle radio and amongst fellow crewmembers. Further, some headsets, such as corded headsets, can restrict the movement of a crewmember's head and reduce the ability to move about the interior of a vehicle.

As vehicle, engine, and transmission soundproofing technologies have advanced, the interiors of many industrial and public safety vehicles have become quieter. Despite soundproofing advancements, the interiors of these types of vehicles are still relatively large and are not completely soundproof, and thus are not conducive to easy communication amongst crewmembers. In addition, cabin speakers that broadcast radio traffic inside of the vehicles may have limitations including distortion, difficult placement, and the risk of being too loud.

Thus, it is advantageous to implement an improved vehicle crew communication system that does not require headsets (although headsets may be used with the system), positions speakers closer to crewmembers than traditional cabin speakers, and allows for verbal communication between crewmembers to be easily detected by a microphone and transmitted. In some embodiments, an individual seat system that incorporates speakers and a microphone that is integrated into the overall vehicle communications system constitutes an improved system. Moreover, in embodiments where the speakers and microphone are in close proximity, there is negligible feedback such that the system provides consistent and coherent communications.

SUMMARY

The present disclosure provides a system and method for feedback cancellation for a vehicle communications system.

According to an embodiment of the present disclosure, a method of cancelling feedback in a vehicle communications system is provided. The method includes receiving a microphone signal from a microphone device, routing the microphone signal over a first signal path and a second signal path, and adjusting a phase and a polarity of the microphone signal on the first signal path to provide an inverted microphone signal having a shifted phase. The method further includes receiving a speaker signal. A component of the speaker signal includes the microphone signal routed over the second signal path. The method further includes modifying the speaker signal by summing the speaker signal and the inverted microphone signal to cancel out at least a portion of the microphone signal component of the speaker signal.

According to another embodiment of the present disclosure, a feedback cancellation electronic circuit for a vehicle communications system is provided. The circuit includes a first circuit path configured to receive a microphone signal provided by a microphone device. The circuit further includes a second circuit path configured to receive the microphone signal provided by the microphone device. The circuit further includes a phase shifter coupled to the first circuit path. The phase shifter is operative to adjust a phase and a polarity of the microphone signal on the first signal path to produce an inverted microphone signal having a shifted phase. The circuit further includes a summing amplifier operative to receive a speaker signal from the second signal path and the inverted microphone signal from the first signal path and to output a modified speaker signal. A component of the received speaker signal includes the microphone signal routed over the second signal path. The summing amplifier is operative to sum the inverted microphone signal and the received speaker signal to cancel out at least a portion of the microphone signal component of the received speaker signal.

According to yet another embodiment of the present disclosure, a vehicle communications system is provided. The system includes a microphone device operative to detect audio and to output a microphone signal based on the audio. The microphone device is positioned proximate a seat of the vehicle. The system further includes an intercom control device operative to receive the microphone signal and to output a speaker signal. A component of the speaker signal includes the microphone signal. The system further includes a seat control station in communication with the intercom control device. The seat control station includes feedback cancellation logic operative to receive the microphone signal. The feedback cancellation logic includes phase shift logic operative to adjust a phase of the microphone signal to produce a modified microphone signal having a shifted phase. The feedback cancellation logic further includes summing logic operative to receive the modified microphone signal and the speaker signal and to sum the modified microphone signal and the speaker signal to cancel out at least a portion of the microphone signal component of the speaker signal.

BRIEF DESCRIPTION OF THE DRAWINGS

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate embodiments of the disclosure, and such exemplifications are not to be construed as limiting the scope of the disclosure in any manner.

DETAILED DESCRIPTION

The present disclosure relates generally to providing communications to the crew of a vehicle with feedback cancellation technology so as to limit the amount of feedback in a communications system. The communications system provides vehicle crewmembers the ability to communicate without the need to wear headsets, although headsets may be used with the communications system as well. Microphones and speakers are illustratively seat-mounted or vehicle-mounted. Moreover, the system incorporates a phase contouring feedback cancellation electronic circuit that allows for a microphone to be placed within close proximity to speakers while reducing or eliminating audible feedback in the communications system. The communications include both radio communications between a vehicle crew and individuals remote from the vehicle and communications between crew members inside and outside the vehicle. While not limited to any particular vehicle, exemplary embodiments relate to industrial vehicles, cranes, military vehicles, marine vessels, and public safety vehicles such as fire apparatus and ambulances, for example.

Figure 1:
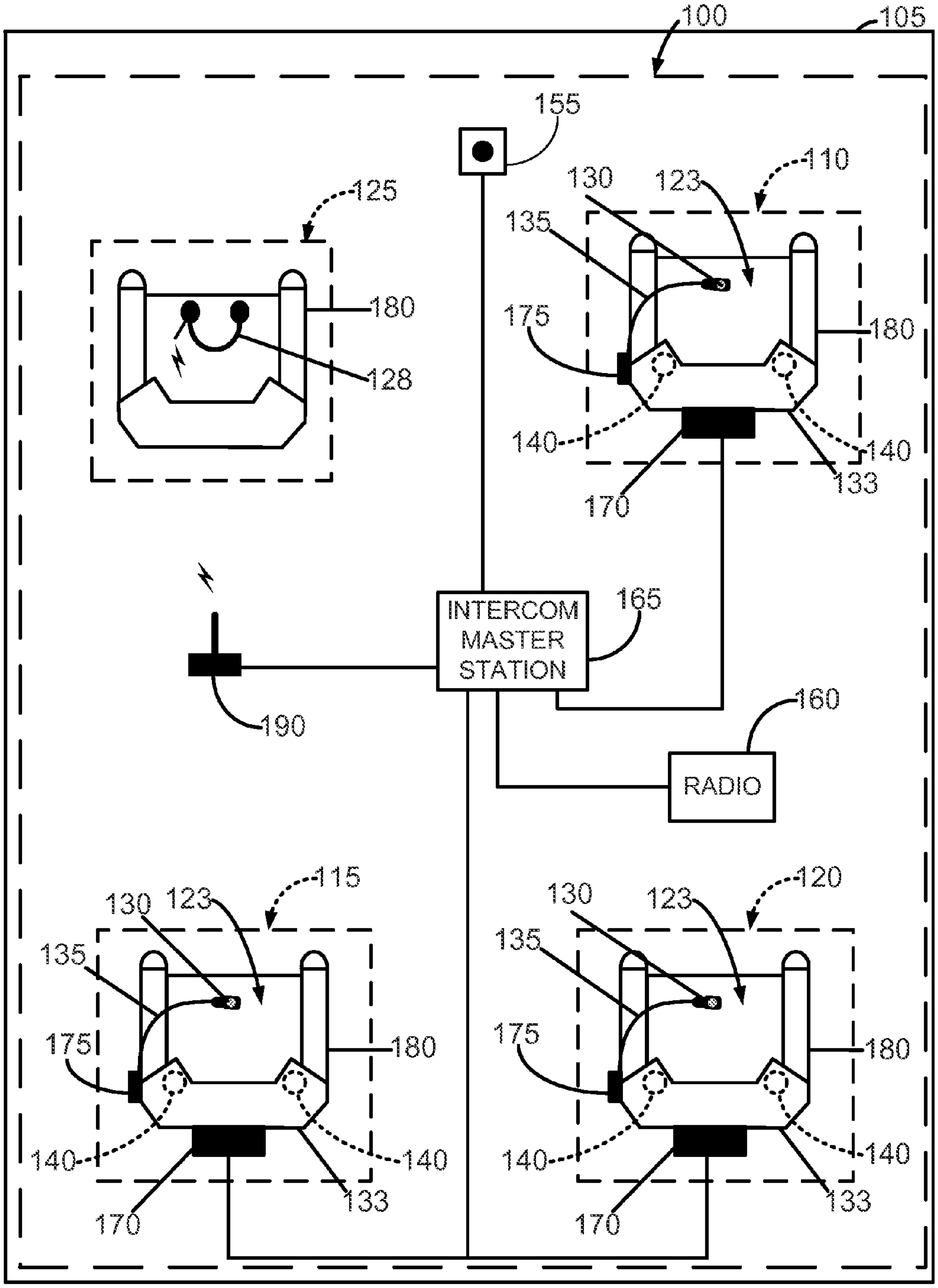
FIG. 1 is a diagrammatic representation of a vehicle with a vehicle crew communications system according to an exemplary embodiment.

FIG. 1 is a top down diagrammatic view of a vehicle 105 with the roof removed and illustrates a vehicle crew communications system 100. Vehicle 105 is illustrated as a truck, although system 100 may be used with other suitable vehicles. For example, the vehicle may be, without limitation, a fire engine, an ambulance, or other public safety vehicle, a crane, a marine vessel, or an industrial truck. Seat positions 110, 115, and 120 are representative individual positions 123 of the communications system 100. Seat position 125 uses a wireless headset 128 to interface into the communications system 100. In this example, position 125 is the driver of the vehicle 105 whom often has to exit the vehicle 105 to perform particular tasks outside of the vehicle 105. The wireless headset 125 allows that member of the crew the flexibility to exit the vehicle 105 and still interface with the communications system 100 within a certain range of the vehicle 105. In one example, wireless headset 125 is operative to communicate with communications system 100 up to two thousand feet away from the vehicle 105. One or more wireless headsets such as headset 125 are optional components of the system 100.

Figure 2:
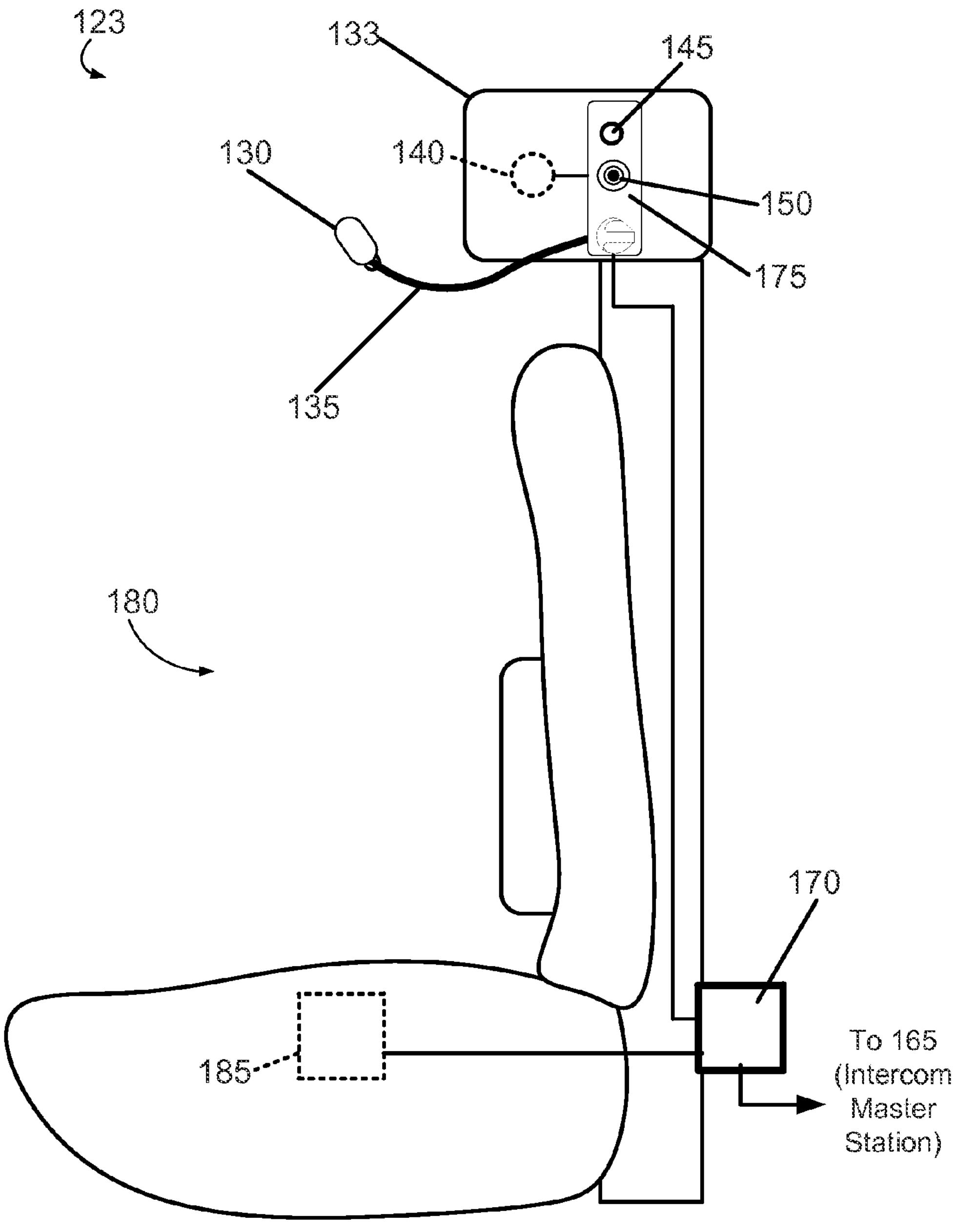
FIG. 2 is a side view diagrammatic representation of an individual seat position.
Figure 3:
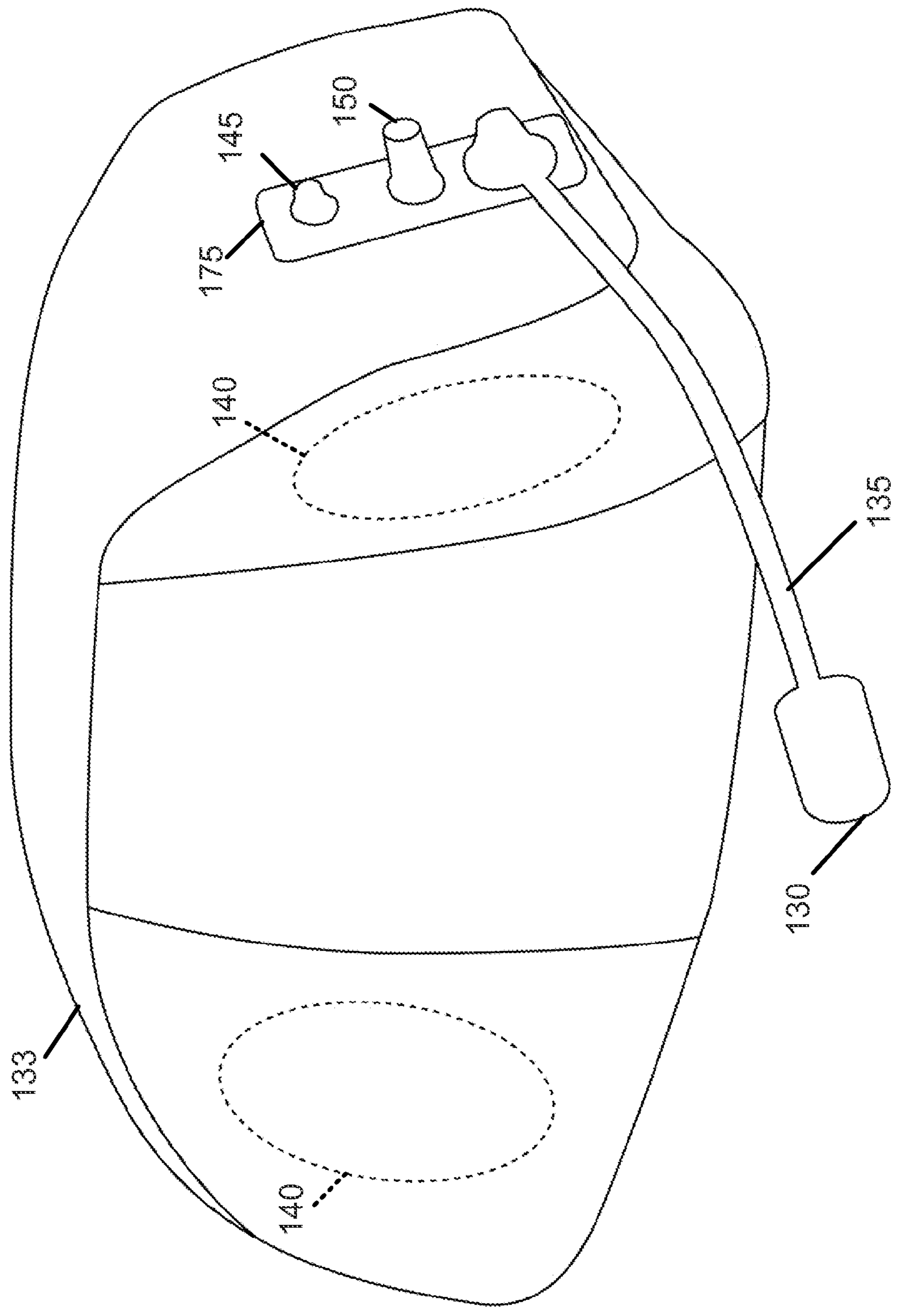
FIG. 3 is a perspective view diagrammatic representation of an individual headrest.

With reference to FIGS. 1-3, seat positions 110, 115, and 120 each have a microphone device 130 mounted to the headrest 133 using a boom 135 to support the microphone 130. Depending on the configuration of the individual positions 123, the boom 135 can be comprised of a number of different types of materials to provide flexibility and adjustability and avoid work hardening of the boom 135. For example, the boom 135 may include two counter wound beryllium copper springs so that the microphone 130 can be placed in front of the crewmember's mouth in a variety of positions and then stay fixed in that position. The boom 135 can also be rotated vertically (up and down) for more adjustability and to allow a crewmember to move the boom 135 out of the way. The length of the boom is adjustable depending on the configuration of the individual positions 123. Other embodiments of the system 100 have the boom mounted in a number of different positions including but not limited to above the crewmember and affixed to a wall of the vehicle 105 or other rigid surfaces around the individual position 123.

The microphone 130 incorporated in each of the individual system positions 110, 115, and 120 may be of several types depending on the kind of vehicle 105 and the noise levels of the interior of the vehicle 105. A preferred embodiment for the microphone 130 incorporates a noise-canceling microphone with a bidirectional pattern that cancels the far field sounds and amplifies the near field sounds. In some embodiments, noise cancelling microphones cancel low frequency noise better than high frequency noise. In the illustrated embodiment, microphones 130 are placed close to the mouth of the crewmember.

Seat positions 110, 115, and 120 each have one or more speakers 140 that are embedded in the inside of the seat headrest 133. Other embodiments can have the speakers 140 mounted in numerous different ways including but not limited to: attached to the exterior of the headrest 133, mounted to the top of the headrest 133, or affixed above or to the sides of the headrest 133. Seat positions 110, 115, and 120 each have a volume control switch 145 (FIG. 2) to allow a crewmember to adjust the volume of the speakers 140 at seat position where he/she is sitting. Seat positions 110, 115, and 120 have push-to-talk (PTT) capability provided by a switch 150 (FIG. 2) coupled to the seat and/or a remotely mounted switch 155 in the vehicle where the crewmember in that seat position can easily access it.

In the illustrated embodiment, individual system position 110, 115, or 120 has a constantly open microphone 130 for hands free communication over the vehicle intercom function of the system and uses the seat PTT switch 150 (FIG. 2) or remote mounted switch 155 to access the radio 160. This mode of operation is called a "Radio Transmit Position" (RTP). In another embodiment, individual system position 110, 115, 120 has no radio 160 access and has an open microphone 130 to communicate over the vehicle intercom function of the system only when the PTT function is activated, such as by depressing and holding down switch 150 or 155. For this individual system position 110, 115, 120, the microphone 130 is closed when switch 150 or 155 is released. This mode of operation is called an "Intercom-only Position" (IOP). In yet another embodiment, individual system position 110, 115, 120 has no radio 160 access and has an open microphone 130 to communicate over the vehicle intercom function of the system only when the PTT function is activated, such as by depressing the PTT switch 150 or 155. In this embodiment, when the PTT switch 150 or 155 is released, the microphone 130 stays open. It is only closed when the PTT switch 150 or 155 is again depressed and released. This mode is called a "Push-on, Push-off Intercom-only Position" (POPO IOP). The RTP, IOP, and POPO IOP positions can be used in any combination in any seat position 123 in the system 100.

The system 100 also incorporates side tone for each individual seat system position 123 and wireless headset 128. Side tone is the sound perception feature that provides audible feedback to a user who is speaking In some embodiments, side tone increases the usability of a communications system and increases the comfort of a user. The side tone circuitry may reside either in an intercom master station 165, a seat position control station 170 or wireless headset 128.

As illustrated in FIGS. 1 and 2, the boom 135, speakers 140, volume control 145, and PTT switch 150 are coupled to a headrest control station 175. The microphone 130 is coupled to the boom 135. The headrest control station 175 is coupled to the seat 180 or mounted nearby depending on the configuration of the vehicle 105 and individual seat system position 123. The headrest control station 175 is coupled to the seat position control station 170.

Referring to FIG. 2, the seat 180 has a seat sensor 185 in some embodiments. The seat sensor 185 is coupled to the seat position control station 170. The seat sensor 185 is used to detect whether a crewmember is in a seat 180 or not. The seat sensor 185 may include a load sensor, a limit switch, or other suitable sensor for detecting the occupied state or the unoccupied state of the seat 180. When a crewmember sits in a seat 180, the seat sensor 185 detects the crewmember and signals the seat position control station 170 that a crewmember is sitting in the seat 180. When a crewmember is sitting in a seat 180, the seat position control station 170 turns on the full functionality of the individual seat system position 123. When an individual seat system position 123 is unoccupied by a crewmember, the seat position control station 170 turns off the functionality of the individual seat system position 123. For example, if an individual seat system position 123 is unoccupied, the functionality is turned off so that there is not a) additional noise introduced into the interior of the vehicle 105 by speakers 140 that are unused, b) extraneous noise put into the vehicle crew communications system 100 by an unused microphone 130, and c) additional power being wasted by an unoccupied individual seat system position 123.

If a seat sensor 185 is detecting that a crewmember is sitting in a seat 180, the seat position control station 170 has a delay circuit for delaying deactivation of the seat system position 123 when the seat sensor 185 no longer detects a crewmember in a seat 180. This delay is so that if the vehicle hits a bump and bounces the crewmember or if a crewmember gets up from the seat momentarily and the seat sensor 185 no longer detects a crewmember sitting in the seat 180, the individual seat system position 123 does not turn off instantly. As an example, if this delay circuit was not present and the vehicle 105 was going through a bumpy section of blacktop, the transmit and receive speech from an individual seat system position 123 may be interrupted numerous times because the crewmember would be bouncing around in his/her seat 180 and turning the seat sensor 185 on and off repeatedly, thus creating a poor user experience and the opportunity for important communications to be missed or not heard. In some embodiments, the delay is three to five seconds but can be adjusted to the time delay required by a specific vehicle application.

As illustrated in FIG. 1, seat positions 110, 115, and 120 are coupled to the vehicle's 105 intercom master station 165 using their individual seat position control station 170. The intercom master station 165 includes a control device that controls the switching of the communications for the vehicle crew communications system 100 for both the intercom traffic and radio traffic. Preferably, more than one individual seat system position 123 can be coupled to the intercom master station 165. For example, up to thirteen positions (wired headset, wireless headset 128, or individual seat system position 123) can be coupled to a single intercom 165, although other suitable configurations may be provided. An exemplary intercom 165 is the Setcom® System 900 manufactured by Pinnacle Peak Holding Corporation of Austin, Tex. A wireless base station 190 is coupled to the intercom master station 165 and is wirelessly coupled to one or more wireless headsets 128.

In the illustrated embodiment, at least one radio 160 is coupled to the intercom master station 165. A radio is not required for the vehicle crew communications system 100 to be operational, and thus the radio 160 is optional. For example, many applications only require communications amongst the crewmembers of the vehicle 105. Thus, the radio 160 is not required in such "intercom-only" applications. The radio 160 is used for communications at long distances from the vehicle 105. Some applications may require more than one radio 160. In such cases, a selector switch may be coupled to the intercom master station 165 and the required radios 160. For example, the Setcom® System 900 intercom master station may incorporate up to three radios in the vehicle crew communications system 100.

Phase Contouring

Seat position control station 170 includes a feedback cancellation circuit 193 (FIG. 4) operative to reduce and/or prevent audible oscillation caused by acoustic feedback between speaker(s) 140 and microphone 130. In many conventional systems, acoustic feedback occurs when the following conditions are met: the microphone 130 is in close enough proximity to the speaker 140 to allow sufficient pickup of the sound produced by the speaker 140; there is sufficient gain (greater than or equal to 1) around the signal loop consisting of the microphone 130 and speaker 140 (this may be, in part, a function of the close proximity); and there is sufficient phase shift such that the signal path phase shift of some frequency through the system is equal to 360 degrees or an integer multiple thereof. In some embodiments, this phase shift is caused by one or more of the following: characteristics of the speaker 140 and microphone 130 and their position in relation to each other; passive circuit elements (resistors, capacitors and inductors) within the signal path; active circuit elements (op-amps and transistors) within the signal path; and the acoustic characteristics of the environment where the microphone 130 and speaker 140 are physically located. Other suitable conditions may results in the acoustic feedback depending on system type and configuration.

In many conventional systems, when these conditions are met, the system will oscillate. In some systems, fewer or additional criteria may be required for the system to oscillate. In some examples, the oscillation is maintained at the maximum power the amplifier can provide to the speaker 140 until the criteria changes. The oscillation may be induced by any input into the microphone 130. Oscillation may occur spontaneously if the criteria are met and there is sufficient acoustic noise in the environment or electrical noise in the speaker and microphone system. In many systems, any signal when the criteria are met will propagate through the system gaining amplitude with each iteration through the signal loop until oscillation is sustained at the maximum power a system is capable of producing. Oscillation will often cease once the input is discontinued.

In an intercom-type communications system where all crewmembers are wearing headsets 128 for communications, all of the various microphone inputs are received by the intercom master station which mixes these signals and amplifies the resulting signal to a level sufficient to drive small speakers which are part of the crew headsets. This speaker signal is sent out over a common lead to deliver to all headsets 128. In this arrangement audible feedback is unlikely because the microphones and speakers may be isolated from each other acoustically by the crewmember's head and headset cups and further by the low level of power delivered to each headset speaker pair. In this arrangement, crewmembers can hear all other crewmembers speaking and can hear their own voice over the intercom speaker feed as well (for the purpose of this document, referred to as side tone).

In the vehicle crew communications system 100 of the present disclosure, the intercom master station 165 receives the various microphone inputs, mixes these signals, and amplifies the resulting signal which is sent out over a common lead to the control stations 170. However, in the individual seat system position 123 there is typically no acoustic isolation between the microphone 130 and speakers 140. The seat position control station 170 is operative to provide additional amplification thereby providing greater audio power than the intercom master station 165 in order to drive the headrest-mounted speakers 140 to a higher volume level. Without the feedback cancellation circuit 193 of the present disclosure, this may lead to feedback if the volume control 145 were set high enough and/or the microphone 130 came into close enough proximity to a speaker 140. Both conditions are often met during normal use of the vehicle crew communication system 100.

Figure 4:
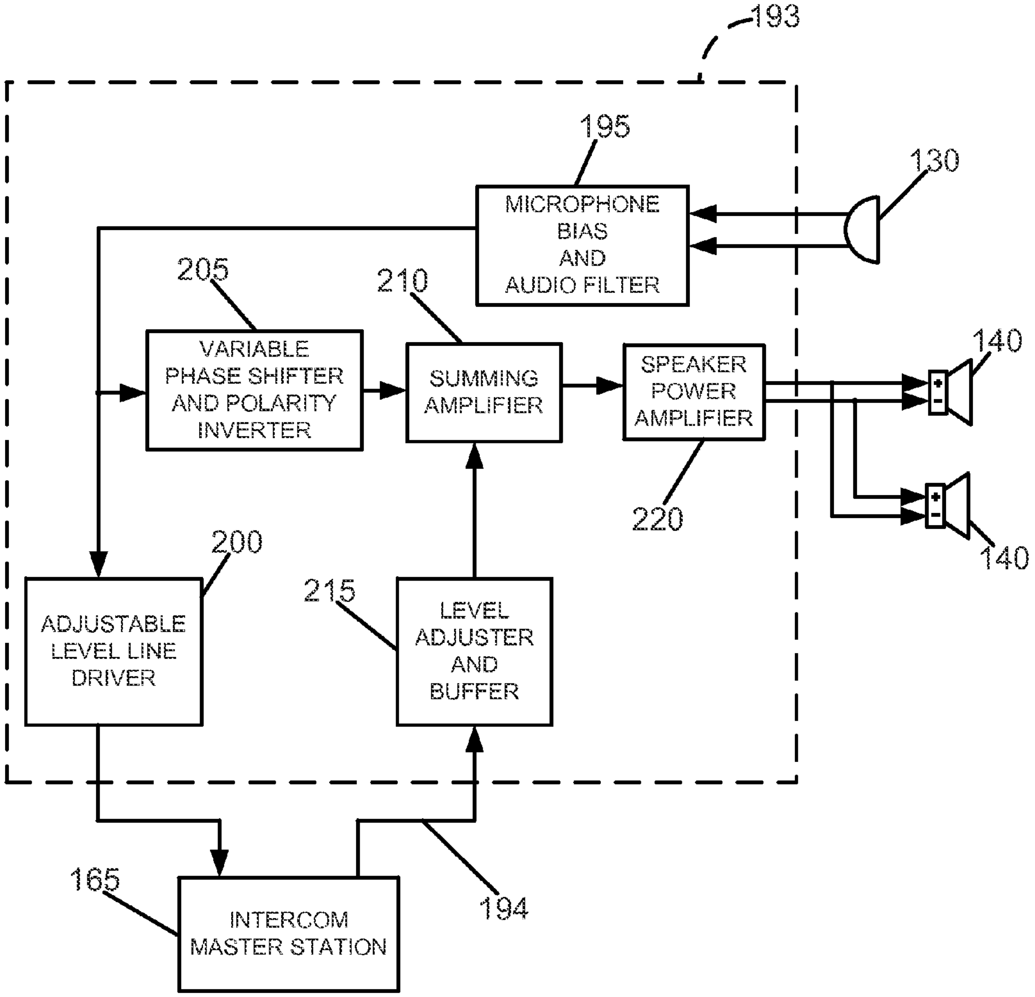
FIG. 4 is a block diagram of exemplary feedback cancellation electronic circuitry that performs the feedback cancellation function.

To accommodate this arrangement of speakers 140 and microphone 130 in the individual seat system position 123, a feedback cancellation circuit 193 of FIG. 4 incorporating a Phase Contouring methodology is implemented in the seat position control station 170 (FIG. 1) to reduce or prevent feedback at the individual seat system position 123.

In operation, audio signals from each microphone in the system, including a wired individual seat system position 123 and/or a wireless base station 190, are summed together in the intercom master station 165, amplified, and sent back out over the common speaker drive lead 194 to the control stations 170 and/or base station 190. The frequency response of this signal chain is relatively flat but is limited in bandwidth, which causes some variation in phase response at the band edges due to the circuit resistances and reactances used for coupling and filtering. Additional phase shift is introduced by the characteristics of the microphone 130 and speaker 140. At the seat position control station 170 the speaker drive signal received over lead 194 is again amplified to drive the speakers 140 in the individual seat system position 123, adding more phase shift to the signal due to the characteristics of the speaker power amplifier 220. The net result of these effects creates a situation where feedback may occur.

As described herein, the feedback cancellation provided with feedback cancellation circuit 193 includes taking a sample of the local microphone signal (of position 123) and summing it with the mixed intercom receive signal being fed to the speaker in a reduced level and of opposite polarity. This causes the audio signal from the local microphone 130 to partially cancel out the same microphone signal which had been sent to the intercom master station 165, amplified and sent back through the common speaker leads. It would have no effect on signals from other microphones from other positions 123 since they are not known to the local microphone 130.

Figure 5:
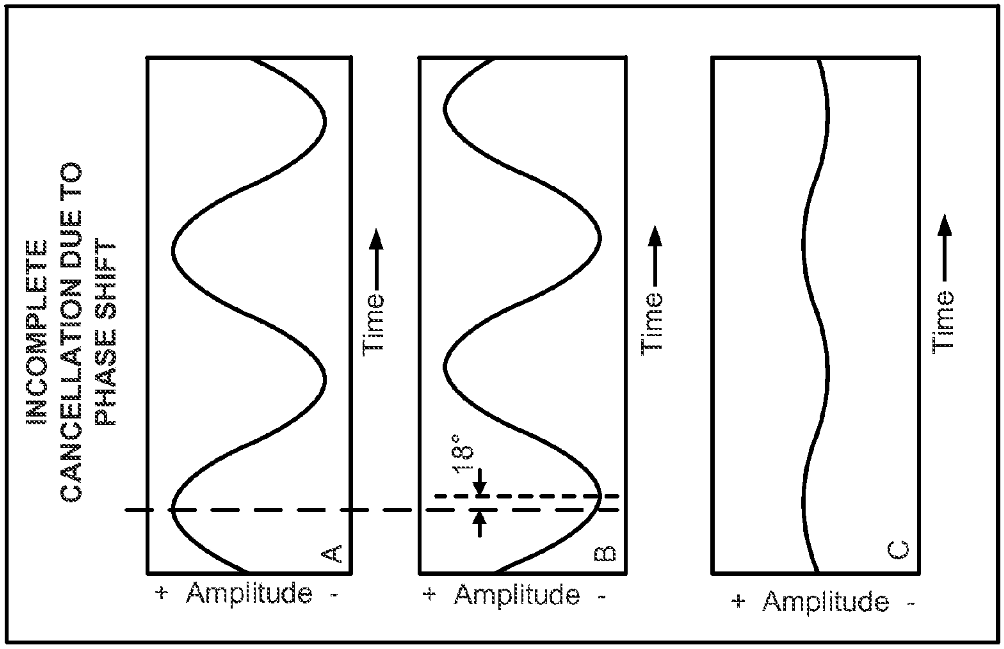
FIG. 5 is a graphical illustration of incomplete signal cancellation due to phase shift.

In some systems, the two signals of the opposing-polarity cancellation scheme have differing characteristics, particularly in terms of phase response. One signal path, in particular the signal path through the intercom master station 165, goes through more circuitry than the other signal path (i.e., the local microphone signal) and accumulates more phase shift than the other signal path. In these systems, the signals are no longer identical at the point in the system where opposing-polarity cancellation is implemented, thus potentially leaving a chance for some given frequency to satisfy the criteria needed for feedback to occur as well as reduced intelligibility. This is illustrated graphically in FIG. 5. In FIG. 5, waveform A represents the local microphone signal and waveform B represents the microphone signal component of the signal through intercom master station 165. Incomplete cancellation is illustrated due to phase shift acquired at a given frequency. Waveform B is an inverse of waveform A, of equal amplitude but with a phase lag of 18 degrees. When waveforms A and B are added together by feedback cancellation circuit 193, there is still a residual signal remaining, waveform C, although at reduced amplitude. With enough system gain, and a microphone close enough to a speaker, this could result in feedback.

In the Phase Contouring method of feedback cancellation of the present disclosure, feedback cancellation circuit 193 is implemented in the design of the seat position control station 170 electronics for compensating for the phase shift. Referring to FIG. 4, audio from microphone 130 is fed to the microphone bias and audio filter 195 in the feedback cancellation circuit 193. At the microphone bias and audio filter 195, gain is applied to the signal as well as frequency response shaping that has a similar response curve to the signal path in the intercom master station 165. From there the signal path is split and sent to both the adjustable level line driver 200 and to the variable phase shifter and polarity inverter 205. The adjustable level line driver 200, which allows the setting of a fixed preset signal level and provides a low-impedance output for driving cables, outputs the microphone signal and sends it to the intercom master station 165. This microphone signal is summed with the other system microphone inputs, amplified, and returned on the common speaker lead 194 from the intercom master station 165 to the seat position control station's 170 feedback cancellation circuit 193 (of each seat position 123). The level adjuster and buffer circuit 215 provides a high-impedance input so as to reduce the likelihood of loading the common speaker drive lead 194 and adjusts the common speaker signal to an appropriate level and sends it on to the summing amplifier 210.

Figure 6:
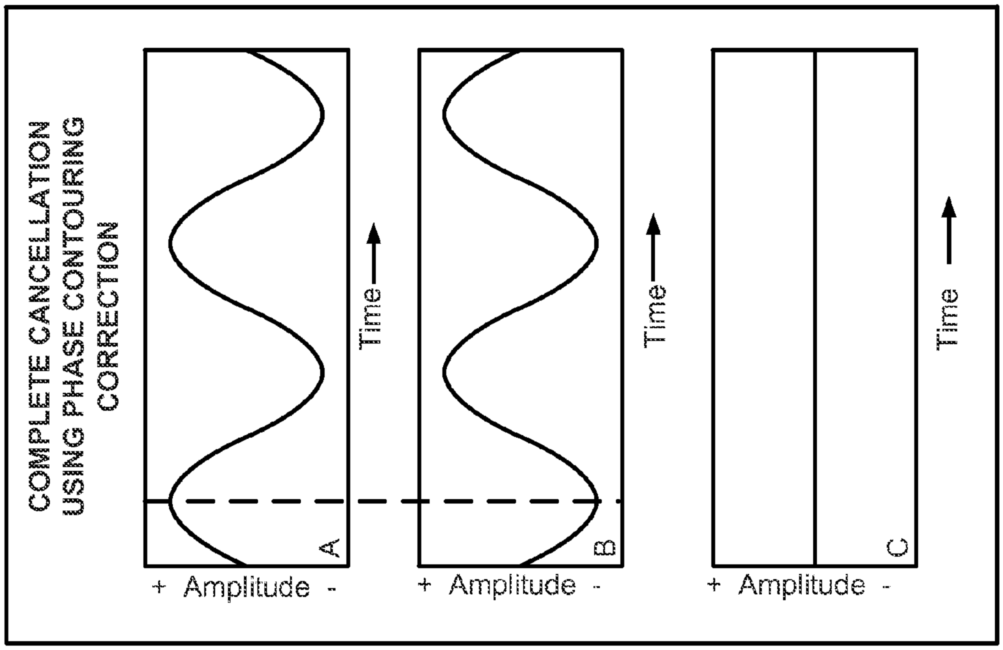
FIG. 6 is a graphical illustration of phase-contoured correction allowing complete or substantially complete signal cancellation.

The variable phase shifter and polarity inverter 205 allows tuning and contouring the phase response, amplitude and polarity of the microphone signal received from microphone bias and audio filter 195, thereby creating a similar but opposite polarity signal with respect to the signal received by the level adjuster 215 and passed on to the summing amplifier 210. This is shown graphically in FIG. 6. In FIG. 6, waveform A is the microphone signal output from the variable phase shifter and polarity inverter 205 and waveform B is the corresponding microphone signal component of the speaker signal from the level adjuster 215. FIG. 6 illustrates complete (or substantially complete) cancellation at a given frequency. Waveform B is illustratively the inverse of waveform A and of equal amplitude but with phase lead or lag having been compensated by variable phase shifter and polarity inverter 205. The summing amplifier 210 sums and amplifies the two waveforms A and B to obtain the waveform C. When waveforms A and B are added together, there is little to no remaining signal as illustrated with waveform C. Thus, a greater degree of cancellation is provided with a phase contouring circuit design of cancellation circuit 193, thereby providing a reduced or eliminated potential for feedback.

With further reference to FIG. 4, feedback cancellation circuit 193 creates a signal at the output of the variable phase shifter and polarity inverter 205 that is, or is close to being, an inverse copy of the same microphone signal that was sent through the intercom master station 165 and returned to the seat position control station 170, by compensating for the phase shifts caused by the intercom audio pathway and any effects of the microphone 130 and speakers 140 themselves. This allows near-complete or complete cancellation of this local microphone component in the speaker signal received from the intercom master station 165 without affecting any other audio signals present from other microphones in the system. The resulting output signal from the summing amplifier 210 is then fed to the speaker power amplifier 220 and out to speakers 140. In some embodiments, the cancellation is adjusted so that some residual level of the local microphone signal remains, allowing the crewmember at this position to have some amount of side tone, but provides robust feedback cancellation for that microphone/speaker pair in individual seat system position 123 by eliminating or reducing the possibility of a loop gain greater than 1 to exist between the microphone 130 and speaker 140 at any system level.

The feedback cancellation circuit 193 improves feedback cancellation by not only providing an inverted copy of a signal, but by providing a means to also compensate for phase shift acquired by the signal as it passes through various elements of a communication system 100, thus allowing much more complete cancellation and providing greater protection against a condition which could cause feedback.

In some embodiments, the cancellation method employs analog circuitry and thus operates real time, so there is no delay or lag in the operation. Alternatively, digital implementations of the cancellation may be provided. However, digital implementations of feedback cancellation may have a finite non-zero response time, often allowing a brief “chirp” sound to be heard before the feedback is fully cancelled.

Figure 7:
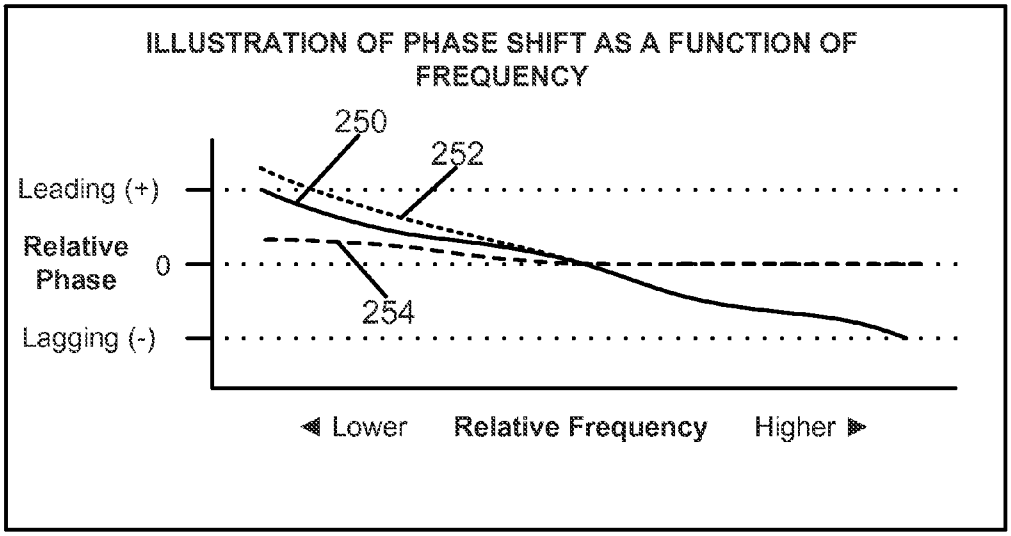
FIG. 7 is a graphical illustration of phase shift of an audio signal through a communications system signal chain.

FIG. 7 is a diagram illustrating a curve 250 of phase shift that may be acquired by an audio signal as it passes through a signal chain, and a curve 252 showing phase shift that may be acquired by the same signal passing through a different signal chain. When the two signals are summed in opposing polarity, without the phase contouring provided with circuit 193, there may be frequencies at which the net phase shift difference through the system is not diminishingly close to zero, and the signals do not cancel completely enough, illustrated by curve 254, and which if supplied enough gain, could still cause a feedback condition, particularly at those frequencies where the relative phase is farthest from 0 degrees.

Figure 8:
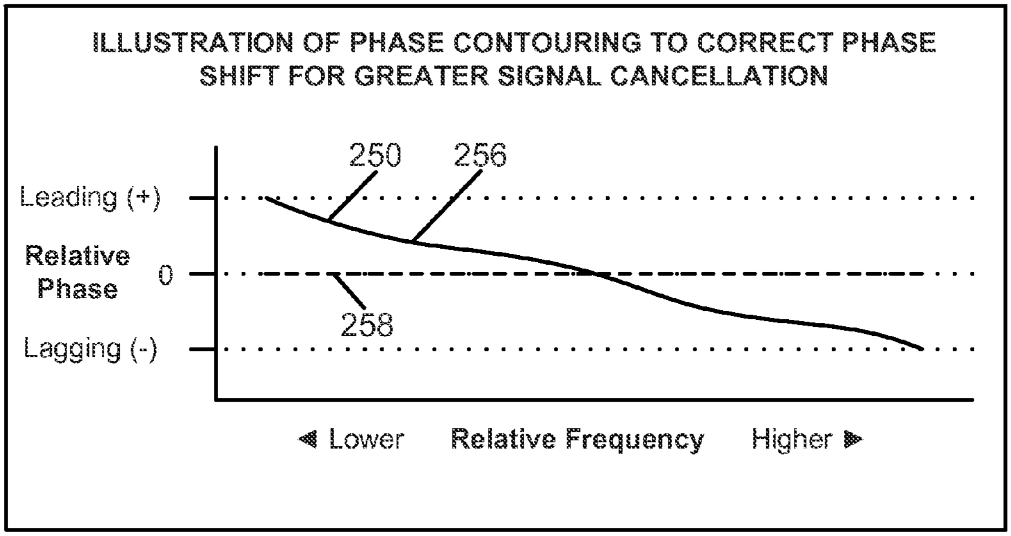
FIG. 8 is a graphical illustration of the action of a phase contouring circuit providing phase shift correction to an audio signal.

FIG. 8 is a diagram illustrating the curve 250 of FIG. 7 as well as a curve 256 of phase shift obtained by passing the original audio signal through a phase contouring circuit (variable phase shifter and polarity inverter 205), to create the curve 256 that is as close as practical to an exact match of the phase response to the curve 250 of FIG. 7. The result is that when the two signals are now summed in opposing polarity, there is minimal phase shift difference (shown by the heavy dashed line 258 at center) between them and there can then be greater cancellation of the signal, substantially or completely eliminating the possibility of a feedback condition.

Exemplary Operations

An exemplary operation is as follows, with reference to FIGS. 1-4. A crewmember enters vehicle 105 and sits down in a seat 180 with an individual seat system position 123. The weight of the crewmember in the seat 180 activates the seat sensor 185 which signals the seat position control station 170 to turn on the individual seat system position 123. With the individual seat system position 123 turned on, the crewmember may hear other crewmembers communicating over the intercom portion of the vehicle crew communications system 100 and any radio 160 communications if there is a radio 160 coupled to the intercom master station 165. Volume of the speaker(s) 140 may be adjusted with the volume control switch 145.

Seat positions 123 each allow a crewmember to verbally speak through the vehicle crew communications system 100 in intercom-mode. A Radio Transmit Position (RTP) 123 has an open microphone 130 so the crewmember needs to have the microphone 130 positioned properly and speak. The crewmember’s voice will then be transmitted to the speaker(s) 140 in other seat system positions 123 and headsets 128 in the system 100. An Intercom-only Position (IOP) 123 has a closed microphone 130 unless the momentary switch 150 is activated and held in the activated position by the crewmember. When the momentary switch 150 is activated, the microphone 130 is opened and allows sound to be passed into the system 100. The crewmember activates the switch 150 and holds it in the activated position and speaks into a properly positioned microphone 130. The crewmember’s voice is then transmitted to the speaker(s) 140 in other seat system positions 123 and headsets 128 in the system 100. A Push-on, Push-off Intercom-only Position (POPO IOP) 123 has either an open or closed microphone 130 depending on the last setting of the POPO switch 150. If the switch 150 is currently in an open state, then the next time it is pressed and released, it will be in a closed state and vice versa. If in a closed state, the crewmember pushes and releases the switch 150 and the microphone 130 opens. If in an open state, the crewmember does not need to press the switch 150. Once the microphone 130 is open, the crewmember speaks into the properly positioned microphone 130. The crewmember’s voice is then transmitted to the speaker(s) 140 in other seat system positions 123 and headsets 128 in the system 100.

Crewmembers in the different positions 123 may also verbally transmit over the radio 160 with the communications system 100. A crewmember in a RTP position 123 presses and holds the switch 150. This action PTTs (activates or keys) the radio 160 and any noise that goes into the microphone 130 is transmitted over the radio 160 including the crewmember’s speech. When the switch 150 is released, the radio 160 stops transmitting and the crewmember’s speech is no longer transmitted. In some embodiments, a crewmember in the IOP position 123 and the POPO IOP position 123 is unable to transmit over the radio 160, but may alternatively be able to talk over the radio in the IOP and POPO IOP positions 123 as with the RTP position 123.

When the crewmember leaves the seat 180, the seat sensor 185 signals the seat position control station 170 that the seat is now unoccupied. The delay circuit in the seat position control station keeps the individual seat system position 123 activated until the delay period has expired. Upon the delay period expiration, the communications of the individual seat system position 123 is turned off.

Several alternative embodiments may be provided, including the following:

A. Split Audio Streams. Instead of a single stream of audio that is transmitted through both speakers 140 in an individual seat system position 123 that mixes multiple streams of radio communications with intercom communications, a split audio system may be provided to split two streams of radio communications and deliver each separate stream to a separate speaker. For example, the split audio intercom system allows for listening to multiple channels, such as both an airport tower and fire dispatch radio channels, at the same time and splits the audio streams into different speakers in the headset. With this system, the vehicle 105 intercom audio stream and the fire dispatch radio audio dispatch are heard in the left ear speaker of the headset and the airport tower radio stream is heard in the right ear speaker. Similarly, with the vehicle crew communications system 100, different audio streams from the different radios 160 and the intercom communication audio streams may be split and directed to the chosen speaker 140.

B. Wireless Connection Between Seat Position Control Station and Intercom Master Station. Instead of the intercom master station 165 being coupled to the seat position control station 170 with a physical cable, an alternative embodiment would have the two devices coupled wirelessly.

C. Voice Activated Microphone Circuitry. In this embodiment, voice activated (VOX) microphone circuitry is incorporated into the vehicle crew communications system 100 for all or any of the individual seat positions 110, 115, and 120 or the wireless headset 128. The VOX circuit provides a noise gate in which a noise level threshold is set for the microphone input level. This threshold level is user adjustable for different ambient noise environments. Any noise below the threshold is disregarded and not passed through the system. A near field noise that is louder than the threshold is allowed to pass through.

D. Wired Headsets Incorporated into the System. Instead of using an individual seat system position 123 or wireless headset 128, a wired or corded headset may be used with the vehicle crew communications system 100. For example, the Setcom® CSB-900 headset manufactured by Pinnacle Peak Holding Corporation of Austin, Tex. is a wired headset that may be coupled to the intercom master station 165.

E. Hybrid Digital/Analog Feedback Cancellation Technique. In this embodiment, a method is provided wherein a feedback condition in the audio pathway is detected by a microprocessor or digital signal processor of circuit 193 analyzing a digitized version of the audio signal, and providing a corrective output to be converted into an analog control signal, fed to a version of the adjustable phase shifter that is capable of being tuned by a control voltage, control current or common digital communication method.

F. Digital Feedback Cancellation Technique (A.) In this embodiment, a method is provided wherein a feedback condition in the audio pathway is detected by a microprocessor or digital signal processor of circuit 193 analyzing a digitized version of the microphone audio signal, and performing the phase shift function on that signal mathematically in the digital domain, converting that correction signal back to an analog signal to be then fed to the summing amplifier 210 for cancellation.

G. Digital Feedback Cancellation Technique (B.) In this embodiment, a method is provided wherein a feedback condition in the audio pathway is detected by a microprocessor or digital signal processor of circuit 193 analyzing a digitized version of both the microphone audio signal and the speaker audio received from the intercom master station 165, performing the phase shift function on the microphone signal mathematically in the digital domain, and performing the subtraction of the microphone signal from the speaker audio signal also mathematically, lastly converting the processed signal back to analog to be fed to the speaker power amplifier 220.

For the embodiments E, F, and G above, such embodiments consist of an accurate digital implementation of the feedback cancellation circuit, so as to overcome the problems encountered with other conventional digital systems which employ techniques such as frequency-shifting and variable frequency-response notch filtering.

The components of feedback cancellation circuit 193 of FIG. 4, including microphone bias and audio filter 195, adjustable level line driver 200, variable phase shifter and polarity inverter 205, summing inverter 210, speaker power amplifier 220, and level adjuster and buffer 215, as well as other components of seat position control station 170 and components of intercom master station 165, include one or more types of logic. In the illustrated embodiment, the logic of feedback cancellation circuit 193 is comprised of analog circuitry operative to implement the functions described herein. The logic may also include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed.

Figure 9:
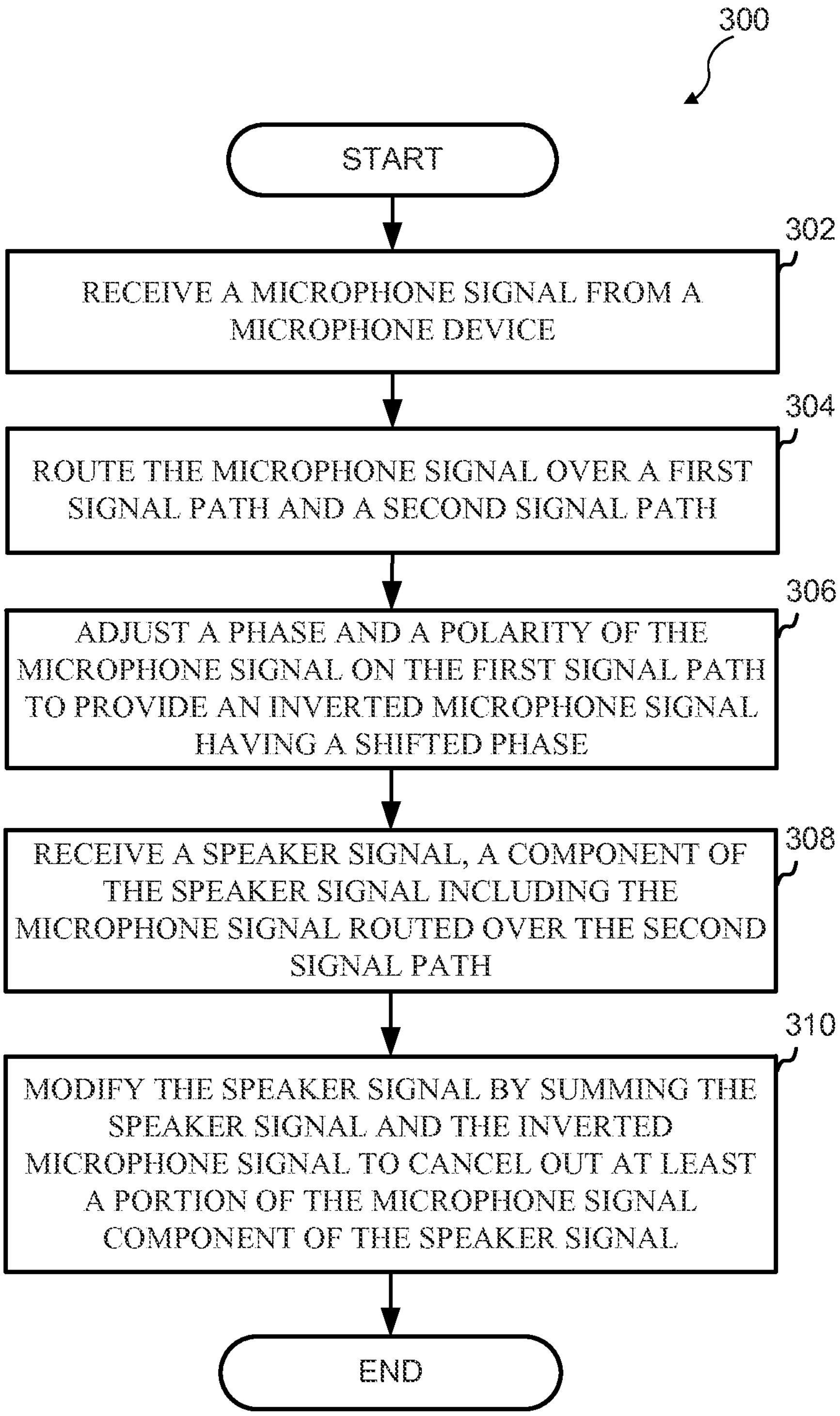
FIG. 9 is a flow diagram of an exemplary method of operation of the feedback cancellation circuitry of FIG. 4.

Referring to FIG. 9, a flow diagram 300 of an exemplary method of operation of feedback cancellation circuit 193 of FIG. 4 is illustrated. Reference is made to FIGS. 1-4 throughout the description of FIG. 9. At block 302, the feedback cancellation circuit 193 of a seat position 123 receives a microphone signal from the microphone device 130 coupled to the seat 180. At block 304, the feedback cancellation circuit 193 routes the microphone signal over a first signal path (e.g., the path from microphone bias and audio filter 195 through phase shifter and polarity inverter 205 to summing amplifier 210) and a second signal path (e.g., the path from microphone bias and audio filter 195 to intercom master station 165 to summing amplifier 210). At block 306, the phase shifter and polarity inverter 205 of the feedback cancellation circuit 193 adjusts a phase and a polarity of the microphone signal on the first signal path to provide an inverted microphone signal having a shifted phase. At block 308, the feedback cancellation circuit 193 receives a speaker signal over the second signal path provided by intercom master station 165. A component of the speaker signal includes the microphone signal routed over the second signal path, as described herein. At block 310, the feedback cancellation circuit 193 modifies the speaker signal by summing, with summing amplifier 210, the speaker signal and the inverted microphone signal to cancel out at least a portion of the microphone signal component of the speaker signal, as described herein.

In some embodiments, the phase of the microphone signal on the first signal path is adjusted such that the shifted phase of the inverted microphone signal substantially matches the phase of the microphone signal component of the speaker signal. In some embodiments, the feedback cancellation circuit 193 adjusts the amplitude of the microphone signal on the first signal path such that the amplitude of the inverted microphone signal substantially matches the amplitude of the microphone signal component of the speaker signal. In some embodiments, the modified speaker signal includes a residual or substantially reduced (or eliminated) level of the microphone signal component. In some embodiments, the feedback cancellation circuit 193 amplifies the modified speaker signal with speaker power amplifier 220 and routes the amplified speaker signal to a speaker device.

While the feedback cancellation circuit of the present disclosure is described in conjunction with seat/vehicle mounted speaker and microphone configurations, the feedback cancellation circuit of the present disclosure is also operative to cancel feedback in other configurations. For example, the feedback cancellation circuit may be utilized in headset configurations or other suitable configurations.

While the embodiments have been described as having exemplary designs, the disclosed embodiments can be further modified within the spirit and scope of this disclosure. This application is therefore intended to cover any variations, uses, or adaptations of the embodiments using its general principles. Further, this application is intended to cover such departures from the present disclosure as come within known or customary practice in the art to which this disclosure pertains and which fall within the limits of the appended claims.

The invention claimed is:

1. A method of cancelling feedback in a vehicle communications system, the method including:

receiving a microphone signal from a microphone device;

routing the microphone signal over a first signal path and a second signal path;

adjusting a phase and a polarity of the microphone signal on the first signal path to provide an inverted microphone signal having a shifted phase;

receiving an audio signal from an intercom control device on the second signal path wherein the audio signal comprises a sum of a plurality of microphone signals and wherein a component of the audio signal includes the microphone signal routed over the second signal path;

modifying the audio signal to provide a speaker signal by summing the received audio signal and the inverted microphone signal having the shifted phase to cancel out at least a portion of the microphone signal component of the audio signal; and routing the speaker signal to at least one speaker device.

2. The method of claim 1, wherein the phase of the microphone signal on the first signal path is adjusted such that the shifted phase of the inverted microphone signal substantially matches the phase of the microphone signal component of the speaker signal.

3. The method of claim 1, further including adjusting the amplitude of the microphone signal on the first signal path such that the amplitude of the inverted microphone signal substantially matches the amplitude of the microphone signal component of the speaker signal.

4. The method of claim 1, wherein the speaker signal includes a residual level of the microphone signal component.

5. The method of claim 1, further including amplifying the speaker signal prior to routing the amplified speaker signal to the at least one speaker device.

6. The method of claim 1, further including:

receiving a plurality of microphone signals from a plurality of microphone devices, the plurality of microphone signals including the microphone signal from the second signal path;

mixing the plurality of microphone signals to generate the audio signal; and transmitting the audio signal over the second signal path.

7. The method of claim 1, further including applying gain and frequency response shaping to the microphone signal prior to the routing the microphone signal over the first signal path and the second signal path.

8. The method of claim 1, further including adjusting a level of the audio signal prior to the modifying.

9. A feedback cancellation electronic circuit for a vehicle communications system, the circuit including:

a first circuit path configured to receive a microphone signal provided by a microphone device;

a second circuit path configured to receive the microphone signal provided by the microphone device;

a phase shifter coupled to the first circuit path, the phase shifter being operative to adjust a phase and a polarity of the microphone signal on the first signal path to produce an inverted microphone signal having a shifted phase; and a summing amplifier operative to:

receive a speaker signal from an intercom control device on the second circuit path wherein the speaker signal comprises a sum of a plurality of microphone signals and wherein a component of the speaker signal includes the microphone signal received by the second circuit path;

receive the inverted microphone signal from the first signal path; and sum the inverted microphone signal having the shifted phase and the received speaker signal to cancel out at least a portion of the microphone signal component of the received speaker signal to provide a modified speaker signal.

10. The circuit of claim 9, wherein the phase shifter adjusts the phase of the microphone signal on the first signal path such that the shifted phase of the inverted microphone signal substantially matches the phase of the microphone signal component of the received speaker signal.

11. The circuit of claim 9, wherein the phase shifter is further operative to adjust the amplitude of the microphone signal on the first signal path such that the amplitude of the inverted microphone signal substantially matches the amplitude of the microphone signal component of the received speaker signal.

12. The circuit of claim 9, wherein the feedback cancellation electronic circuit is an analog circuit.

13. The circuit of claim 9, wherein the modified speaker signal includes a residual level of the microphone signal component.

14. The circuit of claim 9, further including a speaker amplifier operative to amplify the modified speaker signal and to output the amplified speaker signal to a speaker device.

15. The circuit of claim 9, wherein the received speaker signal is provided by the intercom control device in communication with the feedback cancellation electronic circuit, and wherein the plurality of microphone signals are from a plurality of microphone devices.

16. A vehicle communications system including:

a microphone device operative to detect audio and to output a microphone signal based on the audio, the microphone device being positioned proximate a seat of the vehicle;

an intercom control device operative to receive the microphone signal and to output a speaker signal comprising a sum of a plurality of microphone signals wherein a component of the speaker signal includes the microphone signal; and a seat control station in communication with the intercom control device, the seat control station including feedback cancellation logic operative to receive the microphone signal, the feedback cancellation logic including phase shift logic operative to adjust a phase of the microphone signal without adjusting the speaker signal to produce a modified microphone signal having a shifted phase, and summing logic operative to receive the modified microphone signal and the speaker signal and to sum the modified microphone signal and the speaker signal to cancel out at least a portion of the microphone signal component of the speaker signal.

17. The system of claim 16, wherein the intercom control device is operative to receive the plurality of microphone signals from a plurality of microphone devices and to sum the plurality of microphone signals to produce the speaker signal.

18. The system of claim 16, wherein the phase shift logic adjusts the phase of the microphone signal such that the shifted phase of the modified microphone signal substantially matches the phase of the microphone signal component of the speaker signal.

19. The system of claim 16, wherein the phase logic is further operative to adjust the amplitude of the microphone signal such that the amplitude of the modified microphone signal substantially matches the amplitude of the microphone signal component of the speaker signal.

20. The system of claim 16, further including a seat sensor coupled to the seat, the seat control station being in communication with the seat sensor and being operative to detect that the seat is in one of an occupied state and an unoccupied state based on output from the seat sensor, wherein an operation of at least one of the microphone device and the seat control station is disabled in response to the unoccupied state of the seat being detected for a threshold length of time.

* * * * *